United States Patent [19]

Weissmann

[11] Patent Number: 4,788,506
[45] Date of Patent: Nov. 29, 1988

[54] MEASURING PROBE

[75] Inventor: Karl Weissmann, Oftersheim, Fed. Rep. of Germany

[73] Assignee: Pfaudler Company, Rochester, N.Y.

[21] Appl. No.: 785,696

[22] Filed: Oct. 9, 1985

[30] Foreign Application Priority Data

Oct. 13, 1984 [DE] Fed. Rep. of Germany ....... 3437619

[51] Int. Cl.$^4$ ............................................. G01N 27/07
[52] U.S. Cl. .................................. 324/446; 324/65 P; 324/72.5; 324/158 P
[58] Field of Search ............. 324/446, 448, 437, 65 P, 324/65 CR, 447, 158 P, 450, 72.5

[56] References Cited

U.S. PATENT DOCUMENTS

| 2,714,189 | 7/1955 | Ballard, Jr. | 324/450 |
| 4,052,667 | 10/1977 | Schwartz | 324/65 P |
| 4,617,511 | 10/1986 | Shaftel | 324/65 P X |

*Primary Examiner*—Reinhard J. Eisenzopf
*Assistant Examiner*—Robert W. Mueller
*Attorney, Agent, or Firm*—Michael L. Dunn

[57] ABSTRACT

An enamelled or glass coated measuring probe is described, comprising a carrier an electrode fused into an enamelled probe body. The carrier is shaped as a cone out of enamel or ceramic material, into which the electrode or cylindrical metallic body serving for mounting the electrode is fused. In accordance with one embodiment one or several electrodes can be fused into the cone, while in another embodiment the electrode may be exchanged by an electrode out of a different material.

2 Claims, 1 Drawing Sheet

MEASURING PROBE

BACKGROUND OF THE INVENTION

1. Field of the Invention

The present invention relates generally to the field of systems for measuring chemical, electrical and/or physical properties of chemical reactions and more specifically to the field of measuring such, in terms of qualities and/or quantities within chemical reaction process containers.

2. Background

Many chemical reactions, due to their corrosive, erosive, and abrasive nature, are carried out in metal containers, in some cases classified as vessels, which are shielded from the adverse and destructive natures of the chemical reactions by protective coatings. In some situations the vessels are protected by cladding with other metals which are relatively inert to the chemical reactions. In other situations, the vessels are protected with glass or enamel coatings with generally similar inert characteristics.

To measure the ongoing various changes that occur in the chemical, electrical and/or physical properties of the materials undergoing chemical reactions within such vessels, systems have been developed which include interjecting one or more sensors into the chemical reactions. Of course, these sensors are exposed to the adverse affects of the chemical reactions, in the form of elevated or lowered temperatures, and, as stated above corrosion, erosion and abrasion.

Therefore, the sensors have been encased or enclosed in probes which are designed to shield and/or protect the sensors from the adverse affects of the chemical reactions. In particular, measuring probes have been developed which include a sensor, in the form of an electrode, fused within an enamelled or glassed probe body. Such probes are used, for example, to detect pores or flaws in the inert surfaces of the interiors of the chemical reaction vessels, as such develop in the vessels, both initially, when a vessel is phased into service, and throughout the life of the vessel. Another example of the use of such measuring probes is to measure the rH-values and pH-values of the chemical reactions either at discrete intervals or continuously throughout the course of the reactions. Yet other examples of the use of such probes are to measure temperatures, pressures, viscosities, etc., during the course of such chemical reactions.

Due to the necessary sensitivity of the sensors or electrodes included in measuring probes, the enclosures or probe bodies must be exceptionally resistant to the adverse conditions within the reaction vessels. Relatively small defects in the glass or enamel coating may seriously affect the measurements delivered by the probes. Such small defects in the coatings or cladding on the interior surfaces of the chemical reaction vessels might be considered negligible, whereas those same magnitudes of defects would be considered intolerable in the glass or enamel coatings of the probes. Thus, in the heretofore known probes, there were limitations in the degree of temperature differentials and amounts of corrosion, erosion and abrasion that the probe bodies could be subjected to. Also, the life span of the probes bodies has been significantly less than that of the platings or coatings used for the interior walls of the chemical reaction vessels.

There is a need for a measuring probe which can withstand more severe temperature differentials and greater amounts of corrosion, erosion and abrasion in service and which will have an extended life relative to known measuring probes. The present invention provides such a measuring probe.

SUMMARY OF THE INVENTION

The present invention comprises a measuring probe including a probe body, preferably in the form of a cylindrical section, which is coated with glass or enamel on its interior. In one end of the probe body, a hollowed conical section is formed, the surfaces of which are also coated with glass or enamel. A correspondingly shaped and sized ceramic conical section is fitted into the hollow conical section of the probe body. This ceramic conical section, or cone is fused to the glass or enamel coating which coats the hollow conical section of the probe body. An electrode or other sensor element is mounted coaxially through the ceramic cone and fused thereto. This can either be a direct fusion of the electrode or other sensor element to the ceramic of the cone, or alternatively a mounting means can be interposed through the ceramic cone and fused thereto, with the electrode or other sensor element being fixed into the mounting means. It is also possible to mount multiple electrodes or other sensor elements through the ceramic cone such that a variety of different measurements can be taken from a single measuring probe assembly. Also a variety of different shapes, sizes and arrangements of electrodes or other sensor elements can be mounted through a single ceramic cone.

DETAILED DESCRIPTION

Figure 1:
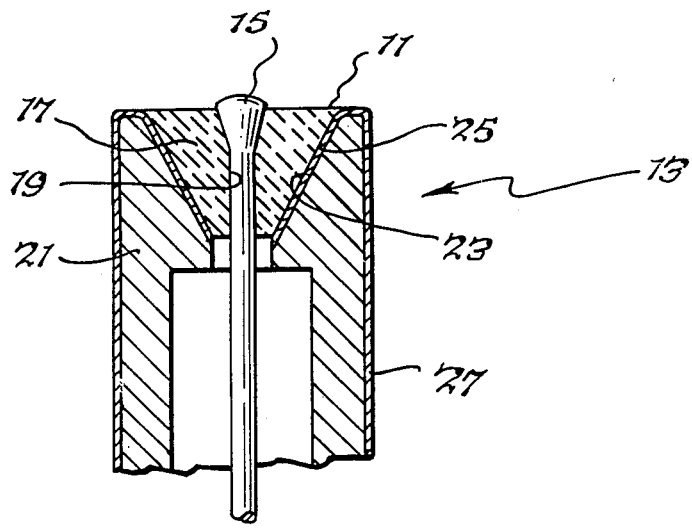
FIG. 1 is a cut-away elevational view of an alternate preferred embodiment of the measuring probe showing a portion of the probe body, the ceramic cone and a sensor element directly fused through the ceramic cone.
Figure 2:
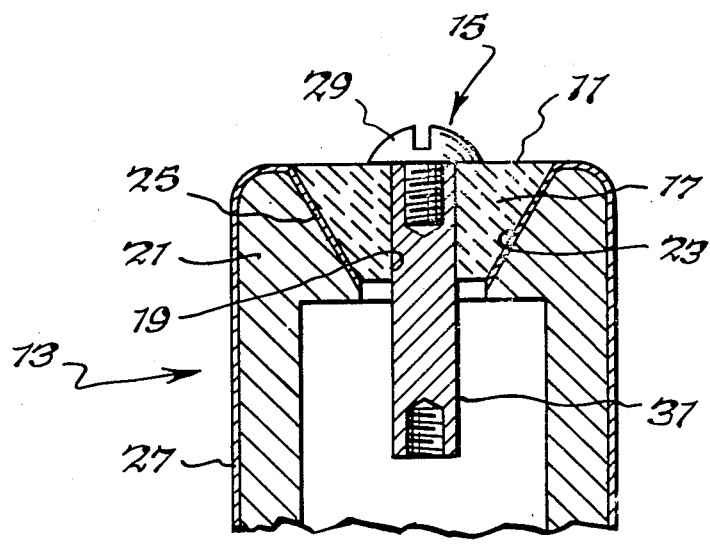
FIG. 2 is a cut-away elevational view of an alternate preferred embodiment of the measuring probe showing a portion of the probe body, the ceramic cone and a different sensor element design, from that shown in FIG. 1, fused through the ceramic cone.
Figure 3:
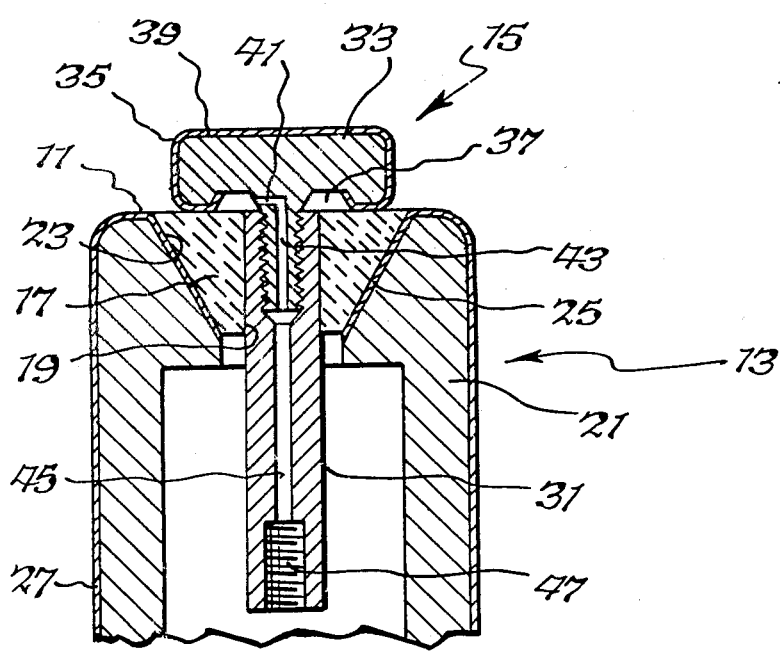
FIG. 3 is a cut-away elevational view of an alternate preferred embodiment of the measuring probe showing a portion of the probe body, the ceramic cone, a sensor element holding means fused through the ceramic cone, and a sensor element mounted to the sensor element holding means.

FIGS. 1 to 3 each show the measurement end 11 of the measuring probe 13 to which the electrode is mounted. The measuring probe may otherwise have any known construction and is glass or enamel coated 27 in the conventional manner.

In the embodiment as shown in FIG. 1 the measuring electrode sensor element 15 is fused through cone 17, which is made from enamel or ceramic material. Cone 17 is shown diverging upwardly to the outside in FIG. 1. The cone 17 is prepared from powder, out of glass or enamel, or preferably out of ceramic material, which powder may be mixed with a binder, if necessary, and then pressed under a pressure between 400 and 1000 times barometric pressure. The pressed body may either be pressed as a cylinder and machined to shape or isostatically passed directly, in the form of a conical section. The pressed bodies are machined (bored) after drying, in order to provide a bore 19 for the electrode sensor element, and for making a true conical shape to mate with the conical bore 23 of the measuring probe 13.

Into the bore 19 the electrode 15 is inserted, which consists in this embodiment out of platinum or another material, which is corrosion-resistant, for the intended use, and which is suitable for fusing in the bore 19 of the cone 17, as will be described afterwards.

When a ceramic material is used, after inserting the measuring electrode 15, the cone 17 is sintered at a temperature between about 700° and 750° C. for two hours. During sintering the electrode 15 is fused in a sealed manner through and to the walls of bore 19. However, in this embodiment certain materials, such as tantalum, are not useable for the electrode 15, if such materials become brittle during sintering, or if the temperature-expansion-coefficient of the material of the electrode 15 and of the cone 17 differ greatly.

If necessary, the cone 17 is precision ground after sintering to predetermined dimensions as mentioned above. Before inserting the sinter cone 17 into corresponding conical bore 23 of the probe body 21, the exterior of the cone 17 is sprayed to add an enamel or glass frit coat 25. After drying the sprayed cone 17 is inserted into the bore 23 of the probe body 21. Before this fusing step the probe body 21 is already pre-coated, as mentioned above, with enamel or glass. The measuring probe 13, in accordance with this embodiment, is first of all usable as a probe for detecting pores or as a probe for measuring the rH-value. The advantages of this construction are: (a) in the case of a corresponding shaping of the cone, by inserting several bores 19, several electrodes 15 can be fused in; (b) the measuring probe remains sealed, even if, as positioned in FIG. 1, corrosion occurs progressing in the downward direction; (c) if the corrosion-resistivity of the ceramic material should not be sufficient, then on the side of the cone 17 exposed to the product an additional corrosion-resistant enamel or glass layer can be applied; and (d) the construction resists high pressures; and the cones 17 can be prefabricated separately from the probe 13.

The embodiment shown in FIG. 2, in which the probe body 21 is also provided with an enamel or glass layer 27, corresponds to the embodiment in FIG. 1 with the exception, that as a measuring electrode 15, a screw 29 is provided, which is screwed into a cylindrical metallic body 31 fused into the cone 17. A specific advantage of this construction is to be seen in the fact that the screw 29, serving as electrode, can be substituted by a screw out of a different material, if the measuring probe should be used for measurements in other corrosive media and/or requiring the use of an electrode out of a different material.

In the embodiment as shown in FIG. 3 elements corresponding to the embodiment in FIG. 2 are provided with the same reference numerals. In this embodiment the fused-in cylindrical metallic body 31 is made out of a material, which is chemically resistant against an electrolyte which may be used. In this embodiment the electrode 15 consists of a screw 33 out of a material which can be enameled or glass coated and which is also resistant against electrolytes. The outer side of the head 39 of this screw 33 is provided with an enamel or glass layer 35, which extends to the underside of the head 39 in order to form a diaphragm 37. In the region of the diaphragm 37, the underside of the head 39 and the upper side of the cone 17 are precision ground and polished to form a seal. The electrolyte is conducted through bores 41, 43, 45 and 47 to the diaphragm 37. The enameled or glass coated probe is especially usable as a pH-measuring probe.

What is claimed is:

1. A measuring probe comprising:
   (a) a hollow probe body, coated on its exterior surface with glass and having a conical bore in one end thereof, said conical bore also being glass coated;
   (b) a conically shaped sintered ceramic insert, shaped and sized to mate with said conical bore of said probe body, said ceramic insert being mated with and fused to said glass coating of said conical bore, said ceramic insert having at least one bore therethrough which communicates with the hollow interior of said probe body;
   (c) at least one electrode means, fused to said ceramic insert through said at least one bore, said at least one electrode means extending from within said hollow interior of said probe body through said at least one bore to the exterior of said ceramic insert.

2. The invention of claim 1 wherein said electrode means comprises:
   (a) at least one cylindrical metal body; fused to said ceramic insert through said bore, said at least one cylindrical metal body which extends from within said hollow interior of said measuring probe through said at least one bore to said exterior of said ceramic insert;
   (b) at least one screw inserted into at least one end of said at least one cylindrical metal body which extends to said exterior of said ceramic insert.

* * * * *